United States Patent [19]

Beier et al.

[11] Patent Number: 5,569,652
[45] Date of Patent: Oct. 29, 1996

[54] DIHYDROSPIRORENONE AS AN ANTIANDROGEN

[75] Inventors: Sybille Beier; Walter Elger; Yukishige Nishino; Rudolf Wiechert, all of Berlin, Germany

[73] Assignee: Schering Aktiengesellschaft, Berlin, Germany

[21] Appl. No.: 162,387

[22] Filed: Dec. 7, 1993

Related U.S. Application Data

[63] Continuation of Ser. No. 835,000, Feb. 14, 1992, abandoned, which is a continuation of Ser. No. 524,396, May 16, 1990.

[30] Foreign Application Priority Data

May 16, 1989 [DE] Germany .......................... 39 16 112.9

[51] Int. Cl.$^6$ .................................. A61K 31/585
[52] U.S. Cl. ........................... 514/173; 514/172
[58] Field of Search ................... 514/173, 172; 540/11, 8

[56] References Cited

U.S. PATENT DOCUMENTS

| | | | |
|---|---|---|---|
| 4,347,245 | 8/1982 | Shapiro | 424/241 |
| 4,502,989 | 3/1985 | Kamata et al. | 552/615 |
| 4,584,288 | 4/1986 | Nickish et al. | 514/172 |
| 4,729,999 | 3/1988 | Young | 514/227 |
| 4,855,289 | 8/1989 | Wester et al. | 514/171 |
| 4,868,166 | 9/1989 | Bittler et al. | 514/173 |

FOREIGN PATENT DOCUMENTS

| | | |
|---|---|---|
| 0 253 607 | 7/1987 | European Pat. Off. . |
| 2652 761 | 5/1978 | Germany . |

OTHER PUBLICATIONS

Breiner et al., "Inhibition of Androgen Receptor Binding by Natural and Synthetic Steroids in Cultured Human Genital Skin Fibroblasts," Klin. Wochenschr., 64:732–737 (1986).

Nishino et al., Arch Pharmacol., vol. 316, R49 (1981).

Nishino et al., Acta Endocrinologica, Suppl. 246, vol. 99, p. 93, Abstract 105 (1982).

*Primary Examiner*—Theodore J. Criares
*Attorney, Agent, or Firm*—Millen, White, Zelano, & Branigan, P.C.

[57] ABSTRACT

Dihydrospirorenone,

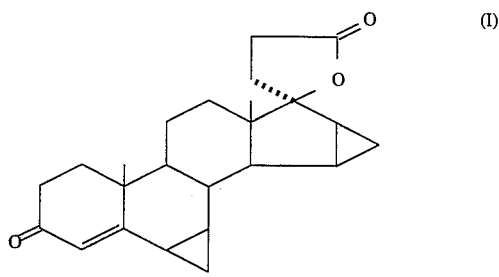

preferably together with an estrogen, can be used for the production of a pharmaceutical agent suitable for treatment of hormonal irregularities during premenopause (menstruation stabilization), for hormonal substitution therapy during menopause, for treatment of androgen-induced disorders and/or for contraception.

27 Claims, No Drawings

DIHYDROSPIRORENONE AS AN ANTIANDROGEN

This application is a continuation of application Ser. No. 07/835,000, filed Feb. 14, 1992, ABN, which is a continuation of Ser. No. 07/524,396, filed May 16, 1990.

BACKGROUND OF THE INVENTION

This invention relates to the use of the compound of formula I

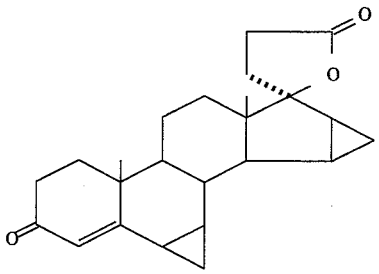

for the production of a pharmaceutical agent.

Compound I (dihydrospirorenone) is described in DE A-26 52 761, among others, as a diuretic of the aldosterone-antagonist type.

It can be seen from DE-A 30 22 337 that compound I, at doses at which the antialdosterone effect already appears, also exhibits a marked gestagen effect. Therefore, compound I can be used alone or in combination with estrogens in contraceptive preparations.

According to DE-A 30 22 337, these preparations are to be used for women who desire contraception and suffer from high blood pressure or in whom blood pressure rises when they take oral contraceptives. Thus, also for women predisposed to increased blood pressure, hormonal contraception is possible.

A combined preparation for substitution therapy and contraception for women before menopause (starting at about age 40) is known from EP-A 0253 607. This combined preparation contains an estrogen from the group 17beta-estradiol, ethynylestradiol and mestranol and a gestagen from the group levonorgestrel, gestodene, desogestrel, 3 ketodesogestrel and norethindrone.

A composition so selected should balance hormonal irregularities in the transition phase of premenopause and help to alleviate the discomfort caused by the hormonal change of the female organism during this phase. Simultaneously, such a composition guarantees the contraceptive protection still necessary at this age.

For various, known reasons and because of the increase in the incidence of contraindications with increasing age, the taking of the usual hormonal contraceptives is recommended for women only until about age 35, so that a hormonal treatment during premenopause and a substitution therapy during menopause using doses that simultaneously have a contraceptive effect can be considered problematic.

Besides these circumstances justifying contraindication, in women of such advanced age, symptoms of androgenization such as, for example, beard growth, deepening of the voice and impure skin are often observed; further, a rise in blood pressure can often be noted.

Thus, there remains a need for good agents for hormonal therapy, especially for such woman, including achievement of one or more of such effects.

SUMMARY OF THE INVENTION

It has now been found that the compound of formula I, in addition to its gestagen and antialdosterone effect, surprisingly exhibits a strong antiandrogenic activity component, and specifically at doses that also make possible the formulation of this compound as an oral contraceptive. Dihydrospirorenone acts as an antiandrogen about as strongly as cyproterone acetate, considered the standard compound (same maximum effect). (Animal model: juvenile, castrated and testosterone-substituted male rat.)

This invention thus relates to the use of the compound of formula I for the production of a pharmaceutical agent suitable for treatment of hormonal irregularities during premenopause (e.g., menstruation stabilization) and/or for hormonal substitution therapy during menopause and/or for treatment of androgen-induced disorders and/or for contraception. Conventional protocols can be used to determine antiandrogenic activity, e.g., as disclosed in Methods in Hormone Research, Editor: R. I. Dorfman, Academic Press, New York, London, 1969, pp. 241; or Androgens and Antiandrogens, Editors: L. Martin and M. Motta, Raven Press, New York, 1977, pp. 163.

Thus, in various aspects, this invention relates to a method of achieving an antiandrogenic effect comprising administering I to a patient in need of antiandrogenic treatment; to a method of treating an androgen induced disorder in a female comprising administering I; to a method of achieving a contraceptive effect in a female during premenopause or menopause (both terms having their conventional meaning, e.g., as shown in "The Controversial Climacteric," P. A. van Keep et al., Ed., MTP Press (1981), e.g., page 9) comprising administering to the female an effective amount of I; to a method of treating gestagen-related hormonal irregularities in a female during premenopause comprising administering I; and/or to a method of achieving gestogen-related hormonal substitution therapy in a female in menopause comprising administering I. In preferred aspects, the females are suffering from and/or predisposed to high blood pressure disorders and/or to androgen-related disorders.

Preferably an estrogen is used together with the compound of formula I. Whether a synthetic or a natural estrogen is preferably used depends on whether the contraceptive effect or the substitutive effect is emphasized: in the first case, ethynylestradiol or another synthetic estrogen is preferred, in the second case, such a pharmaceutical agent should contain a natural estrogen.

But in any case, such a pharmaceutical agent guarantees a woman of middle age (about age 35–55) a stabilization of her menstruation cycle and the contraception still indispensable at this age, with simultaneous, favorable influence on androgen-induced disorders. Of course, this pharmaceutical agent is also suited for younger women, especially for those that have a particular predisposition toward high blood pressure and/or suffer from symptoms of androgenization or are predisposed to one or both of these, e.g., in view of their past medical history, family background, etc., in addition to age.

Here such a use is especially effective because the compound of formula I simultaneously combines a gestagen, antialdosterone effect as well as a strong antiandrogen effect. Previously no substance was known that simultaneously exhibited these three properties.

The dose of the compound of formula I can be 0.5 to 50 mg per day, preferably 1–10 mg per day for all uses of this invention.

Suitable as estrogens are all previously known estrogens. The estrogen used preferably for the various purposes of this invention should be administered in doses such that the estrogen amount used according to the invention is equal to that which corresponds to the administration of 0.02 to 0.04 mg of 17alpha-ethynylestradiol or 0.5 to 4.0 mg of estradiol valerate daily. Such amounts can be conventionally determined using fully conventional tests such as described in Dorfman, supra, page 62. As estrogenic components, among others the 17alpha-ethynyl-estradiol esters and ethers are suitable as well as, for example, esters of 17alpha-ethynyl-7alpha-methyl-1,3,5(10)-estratriene-1,3,17beta-triol (German patent 1 593 509 and German laid-open specification 2 818 164). Further, also the 14,17beta-ethano-14beta-estratrienes described in DE-A 36 28 189 as useful. The estrogenic and gestagenic active components are preferably administered together orally: but they can also be administered separately and/or parenterally or transdermally.

The agents of this invention can be used in the methods of this invention analogously to use of agents known for such purposes, e.g., those of EP 253607 but routinely taking into account the beneficial properties discussed herein.

The formulation of the preparations according to the invention based on 6beta, 7beta; 15beta, 16beta-dimethylene- 3-oxo-4-androstene-[17(beta-1']-perhydrofuran-2'-one (I) is performed in a way known in the art by processing the active ingredient, optionally in combination with an estrogen, with the vehicles, diluents, optional flavorings, etc. common in galenicals, and converting it into the desired form of administration. For the preferred oral administration, tablets, coated tablets, capsules, pills, suspensions or solutions are especially suitable. For parenteral administration, in particular oily solutions, such as, for example, solutions in sesame oil, castor oil and cottonseed oil, are suitable. To increase solubility, solubilizers such as, for example, benzyl benzoate or benzyl alcohol, can be added.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 16 112.9, filed May 16, 1989, are hereby incorporated by reference.

EXAMPLES

Example 1

20.0 mg of 6beta, 7beta; 15beta, 16beta-dimethylene-3-oxo-4-androstene-[17(beta-1')-spiro-5']-perhydrofuran-2'-one and 0.05 mg of 17alpha-ethynylestradiol are mixed homogeneously with 140.45 mg of lactose, 59.5 mg of cornstarch, 2.0 mg of aerosil, 2.5 mg of polyvinylpyrrolidone 25 and 0.5 mg of magnesium stearate and pressed without advance granulation into a tablet of 225 mg final weight.

Example 2

Analogous to example 1, 10 mg of 6beta, 7beta; 15beta, 16beta-dimethylene-3-oxo-4-androstene-[17(beta-1')-spiro-5']-perhydrofuran-2'-one and 0.05 mg of 17alpha-ethynylestradiol with 150.45 mg of 17alpha-ethynylestradiol with 150.45 mg of lactose, 59.5 mg of cornstarch, 2.0 mg of aerosil, 2.5 mg of polyvinylpyrrolidone 25 and 0.5 mg of magnesium stearate are pressed into tablets with a final weight of 225 mg.

Example 3

Analogous to example 1, 20 mg of 6beta, 7beta; 15beta, 16beta-dimethylene-3-oxo-4-androstene-[17(beta-1')-spiro-5']-perhydrofuran-2'-one with 140.5 mg of lactose, 59.5 mg of cornstarch, 2.0 mg of aerosil, 2.5 mg of polyvinylpyrrolidone 25 and 0.5 mg of magnesium stearate are pressed into tablets with a final weight of 225 mg.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of simultaneously achieving, during premenopause or menopause a gestagenic effect, antiandrogenic effect, and an antialdosterone effect in a female patient in need thereof comprising administering an amount of dihydrospirorenone to said female patient, wherein said amount of dihydrospirorenone is effective to simultaneously achieve a gestagenic effect, antiandrogenic effect and antialdosterone effect in said patient.

2. A method according to claim 1, wherein said patient is in premenopause.

3. A method of claim 2, wherein stabilization of menstruation is achieved.

4. A method according to claim 1, wherein said female is of age 35–55.

5. A method according to claim 1, wherein said patient is in menopause.

6. A method according to claim 1, wherein said effective amount of dihydrospirorenone is 0.5–50 mg per day.

7. A method according to claim 6, wherein said effective amount of dihydrospirorenone is 1–10 mg per day.

8. A method of claim 1, wherein said patient is predisposed to androgenization symptoms.

9. A method of claim 1, wherein said patient suffers from or is predisposed to high blood pressure.

10. A method of claim 2, wherein said patient suffers from or is predisposed to high blood pressure.

11. A method of simultaneously achieving, during premenopause or menopause, a contraceptive effect, an antiandrogenic effect, and an anti-aldosterone effect in a female patient in need thereof comprising administering an effective amount of dihydrospirorenone and an effective amount of an estrogenic compound, wherein said effective amount of dihydrospirorenone is effective to simultaneously achieve a gestagenic effect, anti-androgenic effect, and an anti-aldosterone effect in said female patient.

12. A method according to claim 11, wherein said effective amount of dihydrospirorenone is 0.5–50 mg per day and said effective amount of an estrogenic compound is an amount equivalent to 0.5–4.0 mg of estradiol valerate per day.

13. A method of claim 11, wherein said patient suffers from symptoms of androgenization.

14. A method of claim 11, wherein said patient suffers from or is predisposed to high blood pressure.

15. A method of claim 13, wherein said patient is in premenopause.

16. A method of claim 13, wherein said patient suffers from or is predisposed to high blood pressure.

17. A method of claim 11, wherein said estrogenic compound is a synthetic estrogen.

18. A method of claim 11, wherein said estrogenic compound is a natural estrogen.

19. A method according to claim 11, wherein said female is of age 35–55.

20. A method of claim 11, wherein said estrogenic compound is a synthetic estrogen.

21. A method of claim 12, wherein said estrogenic compound is a natural estrogen.

22. A method of claim 11, wherein the estrogenic compound is 17α-ethynylestradiol.

23. A method of claim 11, wherein said patient is in menopause.

24. A method according to claim 11, wherein said effective amount of dihydrospirorenone is 1–10 mg per day.

25. A method of claim 11, wherein said patient is predisposed to androgenization symptoms.

26. A method of claim 15, wherein stabilization of menstruation is achieved.

27. A method according to claim 11, wherein said effective amount of dihydrospirorenone is 0.5–50 mg per day and said effective amount of an estrogenic compound is an amount equivalent to 0.02–0.04 mg of 17α-ethynylestradiol per day.

* * * * *